United States Patent
Hristov et al.

(10) Patent No.: US 9,463,087 B2
(45) Date of Patent: Oct. 11, 2016

(54) DIRECTIONAL TISSUE EXPANDER

(71) Applicant: Mentor Worldwide LLC, Santa Barbara, CA (US)

(72) Inventors: Krasimira Hristov, Belle Mead, NJ (US); Luis Alberto Davila, Alpharetta, GA (US); Anita M. Falcon, Henderson, NV (US); Michael Hoffman, Somerset, NJ (US)

(73) Assignee: Mentor Worldwide LLC, Santa Barbara, CA (US)

( * ) Notice: Subject to any disclaimer, the term of this patent is extended or adjusted under 35 U.S.C. 154(b) by 0 days.

(21) Appl. No.: 14/534,255

(22) Filed: Nov. 6, 2014

(65) Prior Publication Data

US 2015/0272723 A1 Oct. 1, 2015

Related U.S. Application Data

(63) Continuation-in-part of application No. 14/230,251, filed on Mar. 31, 2014.

(51) Int. Cl.
*A61F 2/12* (2006.01)

(52) U.S. Cl.
CPC ............ *A61F 2/12* (2013.01); *A61B 90/02* (2016.02); *A61F 2210/0061* (2013.01); *A61F 2250/0003* (2013.01); *A61F 2250/0018* (2013.01); *A61F 2250/0029* (2013.01); *A61F 2250/0036* (2013.01)

(58) Field of Classification Search
CPC A61F 2/12; A61F 2250/0003; A61M 29/02; A61B 2017/00796; A61B 90/02; A61B 19/24; A61B 2018/00333
See application file for complete search history.

(56) References Cited

U.S. PATENT DOCUMENTS

| 4,574,780 | A | * | 3/1986 | Manders ............... A61B 19/24 128/898 |
| 4,671,255 | A | | 6/1987 | Dubrul et al. |
| 4,863,470 | A | | 9/1989 | Carter |
| 5,026,394 | A | | 6/1991 | Baker |
| 5,104,409 | A | * | 4/1992 | Baker ............................... 623/8 |
| 5,383,929 | A | * | 1/1995 | Ledergerber .......... A61F 2/0077 623/8 |
| 5,447,535 | A | | 9/1995 | Muller |
| 5,496,367 | A | | 3/1996 | Fisher |
| 5,496,370 | A | | 3/1996 | Hamas |
| 6,228,116 | B1 | * | 5/2001 | Ledergerber .......... A61F 2/0077 623/8 |
| 6,605,116 | B2 | | 8/2003 | Falcon et al. |

(Continued)

FOREIGN PATENT DOCUMENTS

| EP | 0197726 B1 | 1/1992 |
| EP | 0963180 | 10/2002 |

(Continued)

*Primary Examiner* — Andrew Iwamaye
(74) *Attorney, Agent, or Firm* — Blossom E. Loo

(57) ABSTRACT

An expandable mammary tissue implant including a shell having an anterior face and a posterior face, the anterior face having an upper pole portion and a lower pole portion meeting at an apex, and an injection zone for receiving fluid therethrough to inflate the implant. The implant further includes a vertical tether member having first and second ends and a central region therebetween having an aperture therethrough. The central region is coupled to the anterior face of the implant at a location such that the injection zone is positioned within the aperture in the central region. The first and second ends of the vertical tether member are coupled to the posterior face of the implant.

10 Claims, 12 Drawing Sheets

(56) References Cited

U.S. PATENT DOCUMENTS

| | | | |
|---|---|---|---|
| 6,743,254 B2 | 6/2004 | Guest et al. | |
| 8,192,486 B2 | 6/2012 | Glicksman | |
| 8,394,118 B2 | 3/2013 | Jones et al. | |
| 8,506,627 B2 | 8/2013 | Van Epps et al. | |
| 2002/0143396 A1* | 10/2002 | Falcon | A61F 2/12 623/8 |
| 2007/0233273 A1 | 10/2007 | Connell | |
| 2009/0198330 A1* | 8/2009 | Kesten et al. | 623/8 |
| 2009/0198331 A1 | 8/2009 | Kesten et al. | |
| 2009/0254179 A1 | 10/2009 | Burnett | |
| 2010/0114312 A1* | 5/2010 | Glicksman et al. | 623/11.11 |
| 2011/0208302 A1 | 8/2011 | Glicksman | |
| 2011/0230964 A1 | 9/2011 | Yacoub et al. | |
| 2011/0301706 A1 | 12/2011 | Brooks et al. | |
| 2014/0077411 A1 | 3/2014 | Schuessler et al. | |
| 2014/0088702 A1 | 3/2014 | Manesis et al. | |
| 2015/0272722 A1* | 10/2015 | Davila | A61F 2/12 623/8 |
| 2015/0327987 A1* | 11/2015 | Schuessler | A61F 2/12 623/8 |

FOREIGN PATENT DOCUMENTS

| | | |
|---|---|---|
| EP | 2387971 A1 | 11/2011 |
| GB | 2021954 A | 12/1979 |
| WO | WO 96/40003 | 12/1996 |
| WO | WO 2004/103196 | 12/2004 |
| WO | WO 2008/154125 | 12/2008 |
| WO | WO 2010/049926 | 5/2010 |
| WO | WO 2011/058550 A1 | 5/2011 |

\* cited by examiner

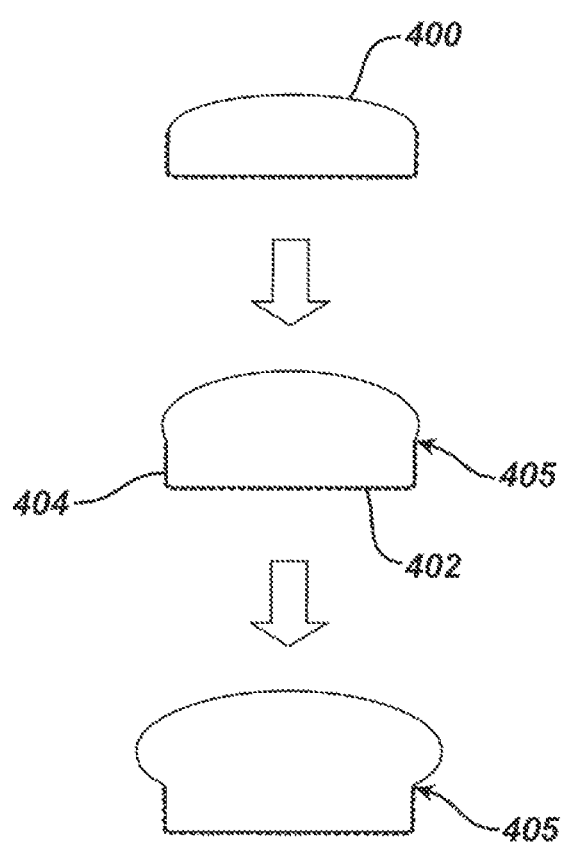

DIRECTIONAL TISSUE EXPANDER

FIELD OF THE INVENTION

The present invention relates generally to the field of expandable implants, and more particularly to expandable mammary implants.

BACKGROUND

Tissue expanders are devices that are implanted beneath the skin and then gradually inflated to stretch the overlying tissue. Such expanders are used to create a pocket for receiving a permanent prosthesis and/or to generate increased skin surface area so that skin can be utilized for grafting or reconstruction.

In the case of mammary implants, tissue expanders are used to create the mammary pocket that will ultimately receive the permanent mammary implant. These expanders are commonly formed of a silicone polymer shell. After implantation, saline or some other fluid is periodically injected into the expander over time, for example through an injection port, until the desired sized pocket is achieved.

With known mammary tissue expanders, as the inflation process continues, resistive pressure from the tissue on the anterior side of the expander can cause the expander to expand in undesired directions (i.e., axially and laterally). In order to minimize the undesired expansion, most surgeons select a smaller expander than needed and over inflate the expander to 200-300% of the rated volume of the expander. This allows the surgeon to utilize the smaller starting foot print of a smaller expander to accommodate for the undesired axial and lateral expansion. Over inflating a smaller expander is undesirable for various reasons. Although expanders are technically tested up to twice their nominal inflation volume, 200-300% inflation could reduce the safety margin of the device. Further, since the foot print is small, at 200-300% inflation the inflated shape is not anatomically correct, but rather is more round or ball-like, which could lead to rotation or flipping over of the implant within the tissue pocket.

Thus, is would be desirable to provide an expandable mammary implant that better provides for the appropriate directional tissue expansion for any given size.

SUMMARY OF THE INVENTION

The present invention provides an expandable mammary tissue implant including a shell having an anterior face and a posterior face, the anterior face having an upper pole portion and a lower pole portion meeting at an apex, and an injection zone for receiving fluid therethrough to inflate the implant; and a vertical tether member having first and second ends and a central region therebetween having an aperture therethrough. The central region is coupled to the anterior face of the implant at a location such that the injection zone is positioned within the aperture in the central region, and the first and second ends of the vertical tether member are coupled to the posterior face of the implant.

According to one embodiment, the vertical tether member further includes first and second posterior face portions adjacent the first and second ends respectively, and first and second vertical portions extending between the central portion and first and second posterior face portions respectively. The entirety of the first and second posterior face portions are coupled to the posterior face of the implant.

In yet another embodiment, the first and second posterior face portions are coupled to the posterior face of the implant at a location such that the first and second vertical portions extend toward the anterior face at an acute angle relative to the first and second posterior face portions.

The vertical tether member may be made of a mesh material, which may be a polyester mesh. The shell may be made of silicone.

In yet another embodiment, the expandable implant further includes a reinforcing material coupled to the shell in a first reinforcement zone that forms at least a peripheral rim portion that extends from a periphery of the posterior face upwardly toward the anterior face by a predetermined distance, and at least one insert member positioned entirely within and extending across an interior of the shell, and coupled to an interior of the shell around an entire perimeter of the insert member at a location substantially adjacent to an upper periphery of the first reinforcement zone.

The insert member may further have at least first and second apertures therein, with the first and second vertical portions of the vertical tether member extending through the respective first and second apertures.

Also provided is an expandable mammary tissue implant including a shell having an anterior face and a posterior face, the anterior face having an upper pole portion and a lower pole portion meeting at an apex, and an injection zone for receiving fluid therethrough to inflate the implant; a reinforcing material coupled to the shell in a first reinforcement zone that forms at least a peripheral rim portion that extends from a periphery of the posterior face upwardly by a predetermined distance, a vertical tether member positioned entirely within the shell and extending between a central region coupled to an anterior face of the shell at a location substantially adjacent to the injection zone and at least a first end coupled to the posterior face, and at least one insert member positioned entirely within and extending across an interior of said shell, and coupled to an interior of said shell around an entire perimeter of said insert member at a location substantially adjacent to an upper periphery of the first reinforcement zone. The insert member has at least a first aperture therein, and the vertical tether member extends through the first aperture.

In one embodiment, the central region of the vertical tether member has an aperture therethrough, and the central region is coupled to the anterior face of the implant at a location such that the injection zone is positioned within the aperture in the central region. The vertical tether member further extends from the central member to a second end that is coupled to the posterior face of the implant.

The insert member may further include a second aperture therein, and the vertical tether member may further extend from the central region through the second aperture to the second end. In yet another embodiment, the first and second ends of the vertical tether member are coupled to the posterior face of the implant and extend both upward and in a lateral direction toward said anterior face. Further, the first and second vertical tether members extend upward and laterally at an acute angle relative to the posterior face.

The insert member and vertical tether members may be made of a mesh material, may be a polyester mesh, and the shell may be made of silicone.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 4a is an exemplary illustration of a possible transition zone between reinforced and non-reinforced portions of a shell;

DETAILED DESCRIPTION

Figure 1:
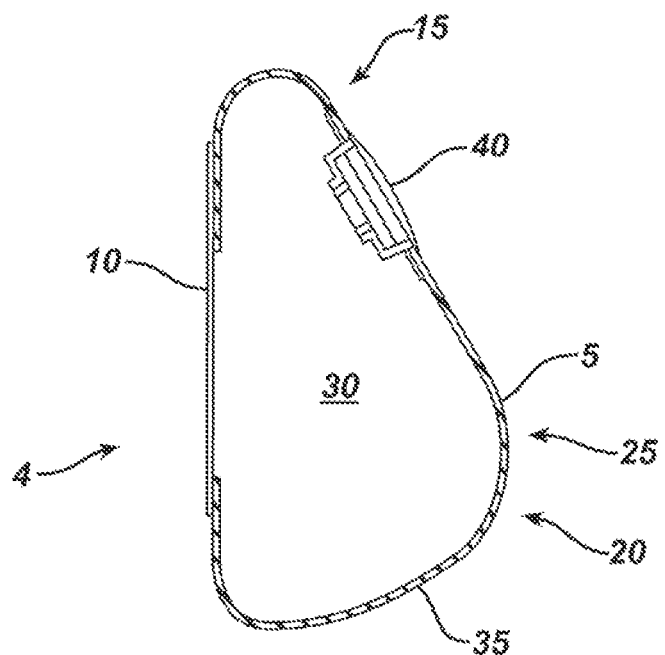
FIG. 1 is a cross-sectional side view an exemplary prior art mammary tissue implant.

FIG. 1 shows a cross-sectional side view of an exemplary prior art mammary tissue expander 4. The expander has a posterior face 10 that lies substantially flat and is placed against a patient's chest wall, and an anterior face 5 that faces outward from the chest wall when implanted. The anterior face 5 includes an upper pole region 15 (i.e., the upper portion of the shell when the implant recipient is standing), a lower pole region 20 (i.e., the lower portion of the shell when the implant recipient is standing), and an apex 25 (corresponding to the point at which the nipple would be in a natural breast) separating the upper pole region and the lower pole region. The outer shell 35 of the expander 5 is typically made of a silicone material and includes an injection port or other valve or self-sealing zone 40 through which saline or another fluid is injected over time into the contained inner region 30. In this manner, the volume of the expander can be increased over time until the desired size pocket is achieved.

With known expanders such as that shown in FIG. 1, although the overall shape of the expander when fully inflated as shown is somewhat anatomically correct, it has been found that when in use within the body, expansion does not occur in an anatomically correct or desired manner. This is because the expander of FIG. 1 is shown in air, and known expanders are designed and tested in air. Due to the minimal resistance of the surrounding air, an expander with an outer shell comprised of a substantially uniform material will expand to the final shape of that shell. In the body, however, the surrounding tissue and muscles counteract expansion, and a device with a substantially uniform outer shell will expand according to the path of least resistance, often determined by the varying resistance of the surrounding tissue. For mammary prostheses, this typically results in deformity of the outer shell to a more pancake like shape, with the anterior projection of the lower pole expansion being less than planned or desired, and lateral and axial expansion more than desired. As indicated previously, in an effort to increase the anterior projection of lower pole expansion, surgeons often pick undersized expanders having a smaller footprint (as against the chest wall), and over inflate them.

The present invention overcomes the problems described above and provides for expansion in the appropriate direction in an appropriate sized implant. More specifically, the implants described herein allow for minimized lateral and vertical expansion, while providing a more anatomically correct profile with less fullness in the upper pole region and more fullness and anterior expansion in the lower pole region. As shown in the illustrative embodiment in FIG. 2, the implant of the present invention includes reinforcement at various locations along the shell to provide for minimal expansion at various desired locations and full expansion at other predetermined locations, to result in an expander that has desired and varied expansion characteristics around its surface area when in actual use within the body.

Figure 2:
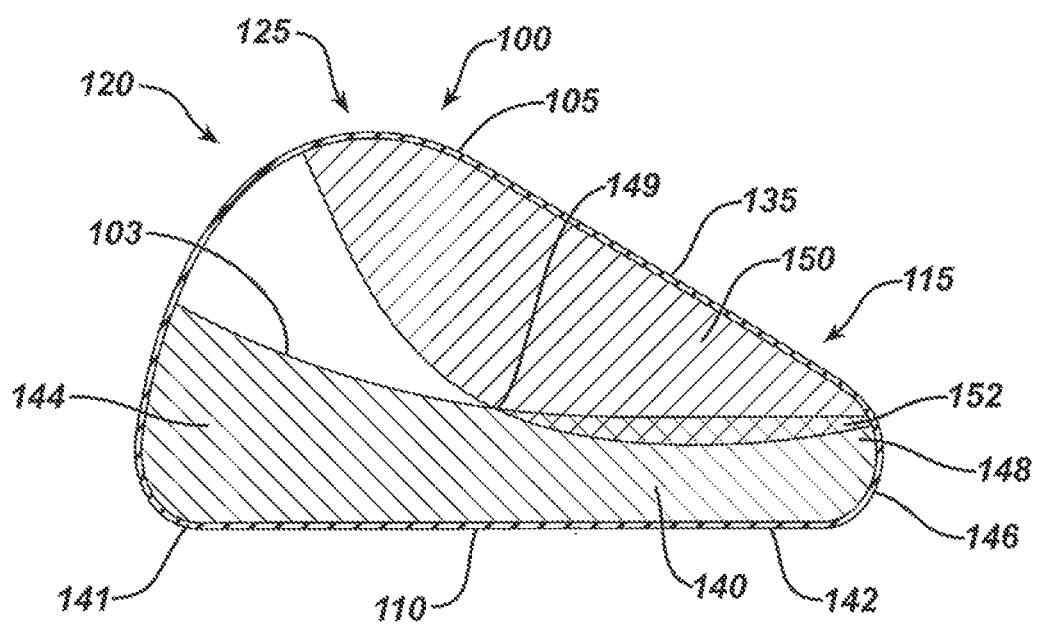
FIG. 2 is a side view of an exemplary mammary tissue implant according to the present invention.
Figure 3:
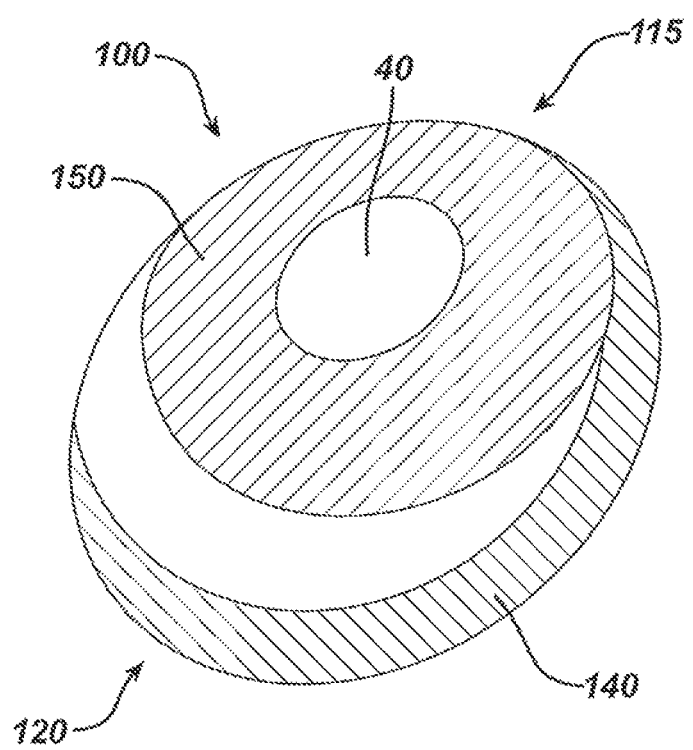
FIG. 3 is a perspective view of the device of FIG. 2.

The expander 100 of FIGS. 2 and 3 similarly includes a posterior face 110 and an anterior face 105 that includes an upper pole region 115, a lower pole region 120, and an apex 125. As indicated previously, the posterior face is substantially flat when the shell is inflated and is the portion of the shell that lies against the patient's chest wall. The posterior face is defined by periphery 141. The expander also includes an injection zone 40. The injection zone may be an injection dome of the well-known type as illustrated in FIG. 1, may be a self-sealing area, or any other suitable device/area through which fluid can be injected and/or removed from the implant.

The outer shell 135 of the expander 100 further includes one or more reinforcement zones, wherein a reinforcing material limits the expandability of the outer shell material. According to one embodiment, the outer shell is made of silicone, and the reinforcing material is a mesh, such as a polyester mesh, although any suitable implantable mesh may be used. Alternatively, the reinforcing material may be a silicone sheet having an elasticity equal to or lower than the elasticity of the shell. The area of the shell having a reinforcing material coupled to it will have an overall elasticity less than any unreinforced area regardless of the elasticity of the reinforcing material. In a preferred embodiment, however, the reinforcing material has elasticity that is substantially lower than the elasticity of the shell.

Further, any other suitable material may be used that adequately functions to restrict expansion of the shell by having an elasticity that is equal to or less than that of the shell material. Exemplary other materials include silicone based polymers, composite materials, polyurethane, polypropylene, and other biocompatible polymeric materials. The reinforcing material may be coupled to the shell by covering the mesh with an un-vulcanized silicone sheet and pressing it into the shell such that the un-vulcanized silicone sheet essentially acts as a glue. The strength of the formed connection can be improved by curing the silicone at an elevated temperature over a period of time (i.e., 315-350 degrees Fahrenheit for approximately 30 minutes).

The embodiment of FIG. 2 includes a first reinforcement zone 140 and a second reinforcement zone 150, both of which are illustrated with cross-hatching. The first reinforcement zone 140 has a first end 146 and a second end 144, and includes at least a peripheral rim portion 148 that extends from the periphery 141 of the posterior face 110 upward into the anterior face 105 by a predetermined distance to an upper periphery 103. The predetermined distance may be constant around the periphery, or may vary along the periphery as shown in FIG. 2. The first reinforcement zone may further extend so as to coincide with the entirety of the posterior face, or some portion thereof. The first reinforcement zone 140 restricts lateral and axial expansion of the shell in the peripheral area immediately adjacent to the posterior face. In this manner, the surgeon need not choose an expander having a smaller posterior face than desired in order to account for undesired lateral expansion around the perimeter of the base of the implant.

The embodiment of FIG. 2 further includes a second reinforcement zone 150. A first end 152 of the second reinforcement zone preferably substantially abuts or overlaps a first end 148 of the first reinforcement zone 140 so that the upper pole region 115 of the expander is entirely reinforced as between the first and second reinforcement zones. In this manner, upon being infused with fluid, the expander is unable to appreciably expand in the upper pole region. The second reinforcement zone extends from the first end 152 and along at least a portion of the anterior face region 105 of the expander, essentially forming a reinforced "hinge" like structure centered around the upper pole region 115, and having hinge points 149 on both sides where the first and second reinforcement zones first meet and start to overlap or abut each other. In certain embodiments, the reinforcement material covers from about 25% to about 80% of the shell surface area, and more preferably from about 50% to about 75% of the shell surface area.

In this manner, expansion of the upper pole region beyond the intended shape is restricted, while more freely allowing desirable expansion of the lower pole region 120. In one embodiment, the second reinforcement zone extends substantially to the apex 125 of the shell.

Although the embodiment above is described as having first and second pieces of reinforcing material, one skilled in the art will readily understand that the reinforcement zones can be established with a single piece as well.

In a further aspect of the present invention, the reinforcing material may be designed so that the degree of elasticity of the material varies at different locations. With a uniform reinforcing material, particularly when the elasticity of the reinforcing material is much different than that of the shell, it may be the case that somewhat sharp transition zones appear between the reinforced regions of the shell and the unreinforced regions. An exemplary illustration is shown in FIG. 4a, wherein the implant shell 400 is reinforced along the posterior face 402 and a peripheral region 404 similar to that described above. The difference in elasticity between the shell material and the reinforced zone may cause a sharp transition at the point 405 where the reinforced shell meets the unreinforced shell as demonstrated in FIG. 4a with an implant shell shown in three stages of inflation. To minimize this possible effect, the reinforcing material may have varying elasticity properties at different locations, or simply have an elasticity gradient (gradually decreasing or increasing elasticity properties) in a given direction. In a preferred embodiment, elasticity of the reinforcing material increases in the direction towards the areas which are free of reinforcing material, or have less reinforcing material, so that the reinforcing material immediately adjacent the non-reinforced areas has the highest elasticity. This can be accomplished by various means including, for example, providing apertures in the reinforcing material that vary in size and/or density along the length of the material. Exemplary embodiments are shown in FIGS. 5a-5c, with FIG. 5a illustrating circular apertures of varying diameter 500a along the length of the material, and FIGS. 5b and 5c illustrating varying slit-like aperture arrangements 500b, 500c along the length of the material. Further, the thickness of the mesh or other material may vary along the length to achieve this result. In another embodiment, both varying aperture size and/or aperture density (i.e., the number of apertures in a given area) along the length of the material and/or simultaneously varying thickness along the length of the material are contemplated to provide the desired elasticity gradient.

Figure 4B:
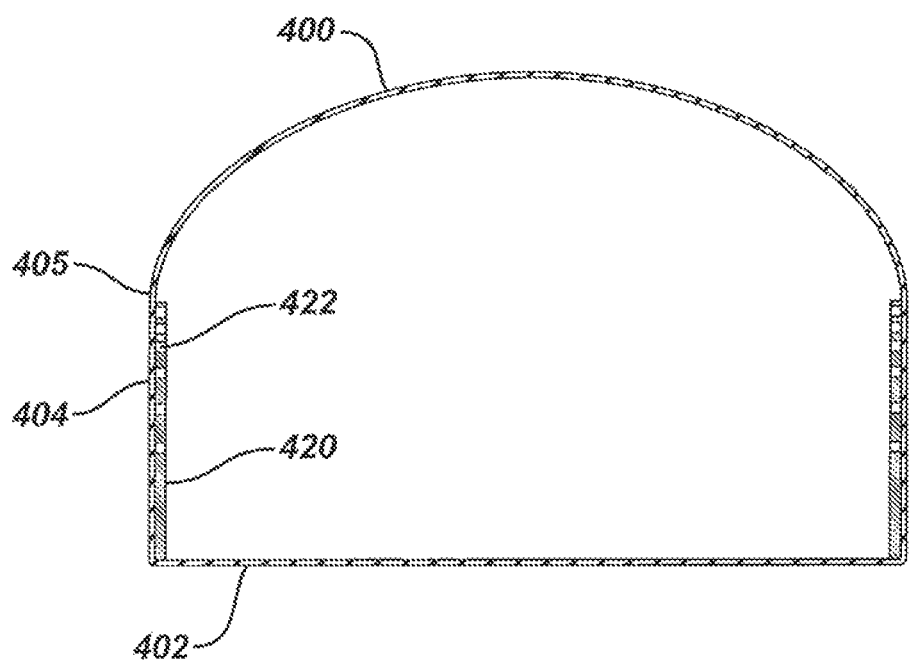
FIG. 4b illustrates the mammary implant of FIG. 3 further including a reinforcing material having varying elastic properties.
Figure 5A:
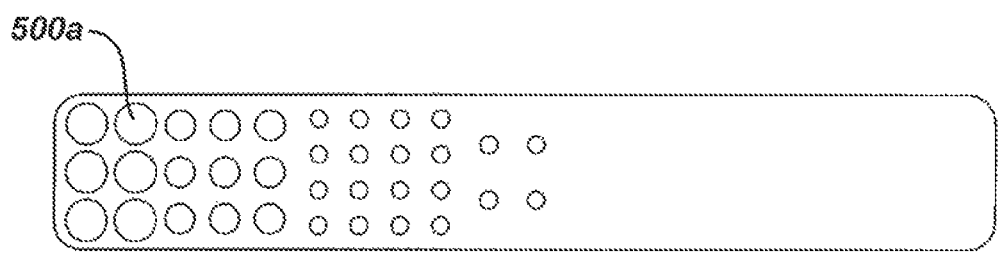
FIGS. 5a-5c illustrate exemplary embodiments of a reinforcing material having varying elastic properties along its length.
Figure 5B:
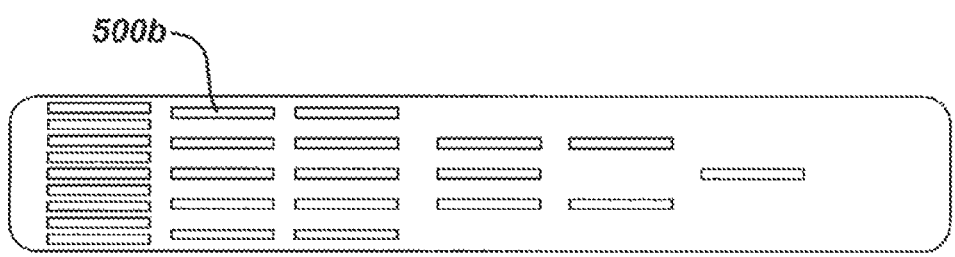
Figure 5C:
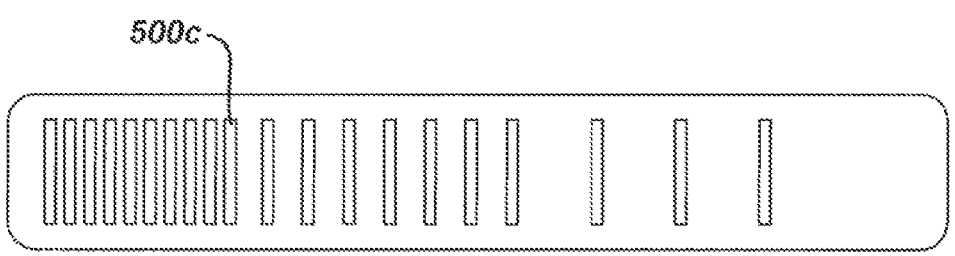

FIG. 4b illustrates the implant shell 400 having reinforcing zone 420 with a lower elasticity proximal to the posterior face 402 and a higher elasticity in the peripheral region 404, with elasticity increasing due to higher density of apertures 422 cut in the material 420. As can be seen from FIG. 4b, elasticity is higher closest to the transition point 405 where the reinforced shell meets the unreinforced shell.

Figure 6A:
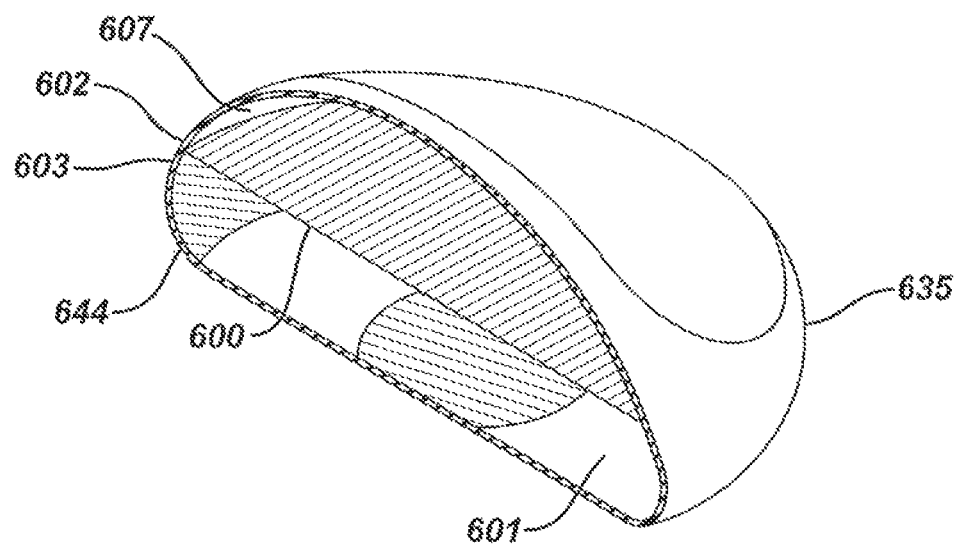
FIG. 6a is a cross-sectional, perspective view illustrating a mammary tissue implant according to the present invention including an insert member.
Figure 6B:
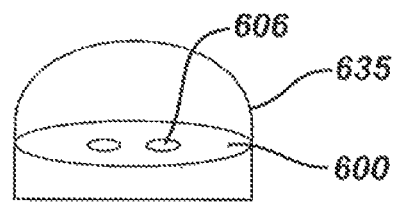
FIG. 6b illustrates an alternate configuration for a mammary implant having an insert member.

In yet another embodiment of the invention, the device illustrated in FIGS. 2 and 3 may further include an additional, separate reinforcing insert member 600 as illustrated in FIGS. 6a and 6b. The insert member is positioned entirely within the interior space 601 of the shell 635. In the illustrated embodiment, the insert member is sized and shaped to span the entire interior or the shell and is secured to the interior surface 607 of the shell around its entire periphery 602, preferably at a location substantially adjacent to the upper periphery 603 of the first reinforcement zone 644. The insert member helps minimize undesired effects at a transition zone of the type described above, and further assists in maintaining the desired shape of the implant during expansion. The insert member may further include holes, apertures or the like 606, as illustrated in FIG. 6b, in order to allow movement of fluid within the shell as it is expanded. In alternate embodiments, the insert member may be in the form more of a "tether" or the like, such as a strip (or multiple strips) extending across the interior of the shell at any desired location, rather than having a configuration that substantially spans the entire interior. The insert member may be formed of any suitable material having an elasticity that is suitable to increase the shell's resistance to outward expansion, such as Dacron™, polypropylene, Dacron™-silicone composite etc. The insert member may be secured to the inside of the shell using un-vulcanized silicone sheeting and heat, silicone based adhesives, solvent-based bonding, diffusion bonding, ultrasonic welding, laser spot welding, and other techniques known to a skilled artisan.

Figure 6C:
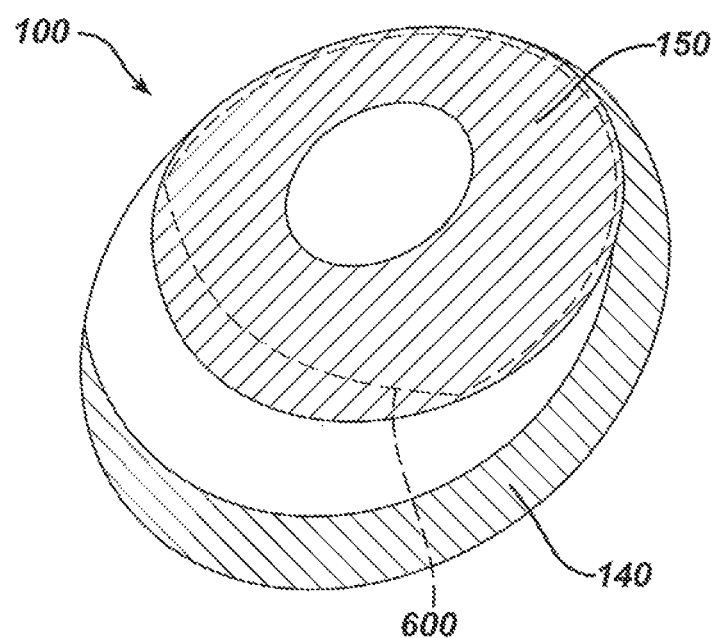
FIGS. 6c and 6d illustrate the mammary implant of FIG. 3 and further including an insert member.
Figure 6D:
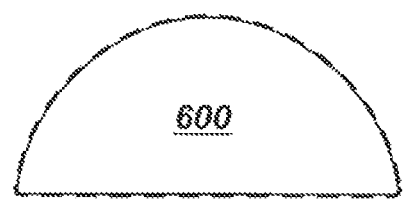

FIGS. 6c and 6d illustrate the implant of FIG. 3 having alternate insert member 600 therein. In this embodiment, the insert member (shown in dotted lines in FIG. 6c) is positioned in a substantially similar manner as illustrated in FIGS. 6a and 6b, but has an alternate "half-moon" type shape, as shown clearly in FIG. 6d.

Figure 6E:
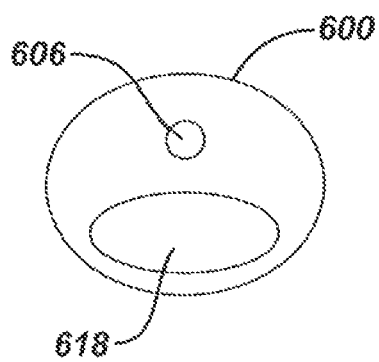
FIGS. 6e-6h illustrate various alternate embodiments of insert members.
Figure 6F:
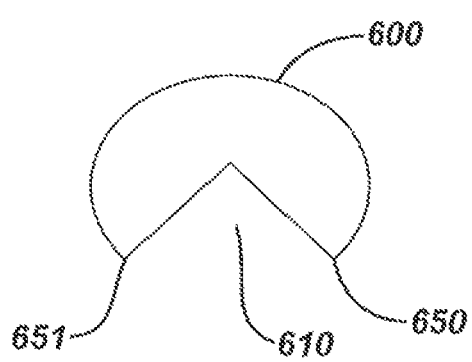
Figure 6G:
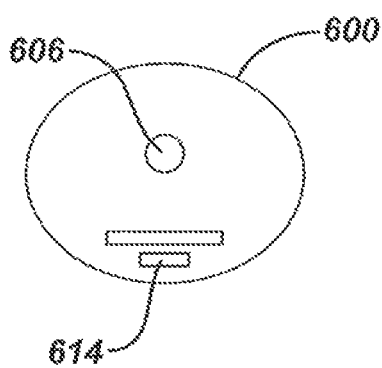

The reinforcing insert member 600 may have various other shapes and configurations, examples of which are shown in FIGS. 6e-6h. In FIG. 6f, the insert member 600 has a cutout 610 generally shaped/positioned so that its first and second points 650, 651 correspond to or substantially align with the hinges 149 where the first and second reinforcement zones begin to overlap (see FIG. 2). In FIG. 6e, the insert member 600 has a large size aperture 618 which is generally shaped/positioned so as to correspond to the location of the hinges. The size and location of large size aperture 618 are selected to locally increase elasticity of insert member 600, with area of the large size aperture 618 being from about 20% to about 40% of area of insert member 600, most preferably from about 20% to about 30% of area of insert member 600. FIG. 6g illustrates an insert member 600 with at least one optional aperture 606 and an array of slits 614 providing for increased elasticity of the insert member 600. The array 614 is generally shaped/positioned so as to correspond to the location of the hinges.

Figure 6H:
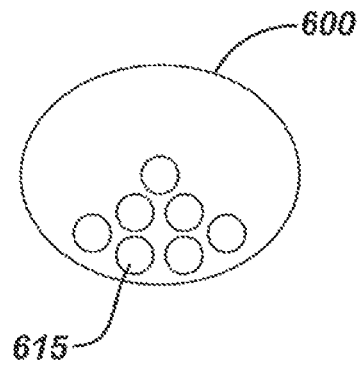

Finally, FIG. 6h illustrates an insert member 600 having a plurality of apertures 615 providing for increased elasticity of inset member 600, with apertures 615 generally shaped/positioned so as to correspond to location of hinge point as described previously.

Figure 7A:
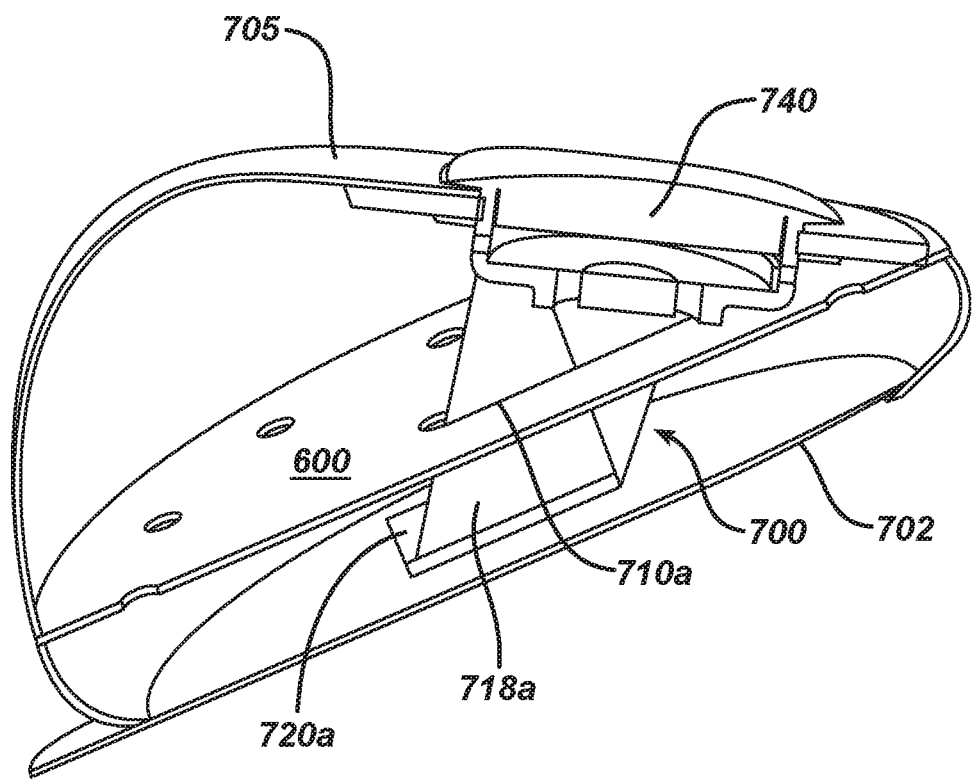
FIGS. 7a and 7b illustrate cross-sectional perspective and side views respectively of an alternative embodiment having a vertical tether member.

Yet another embodiment according to the present invention is shown in FIGS. 7a-7d, which includes a vertical tether member 700 extending entirely within the interior of the implant between the posterior face 702 and the anterior face 705, as shown in the cross-sectional view of FIG. 7a.

Figure 7B:
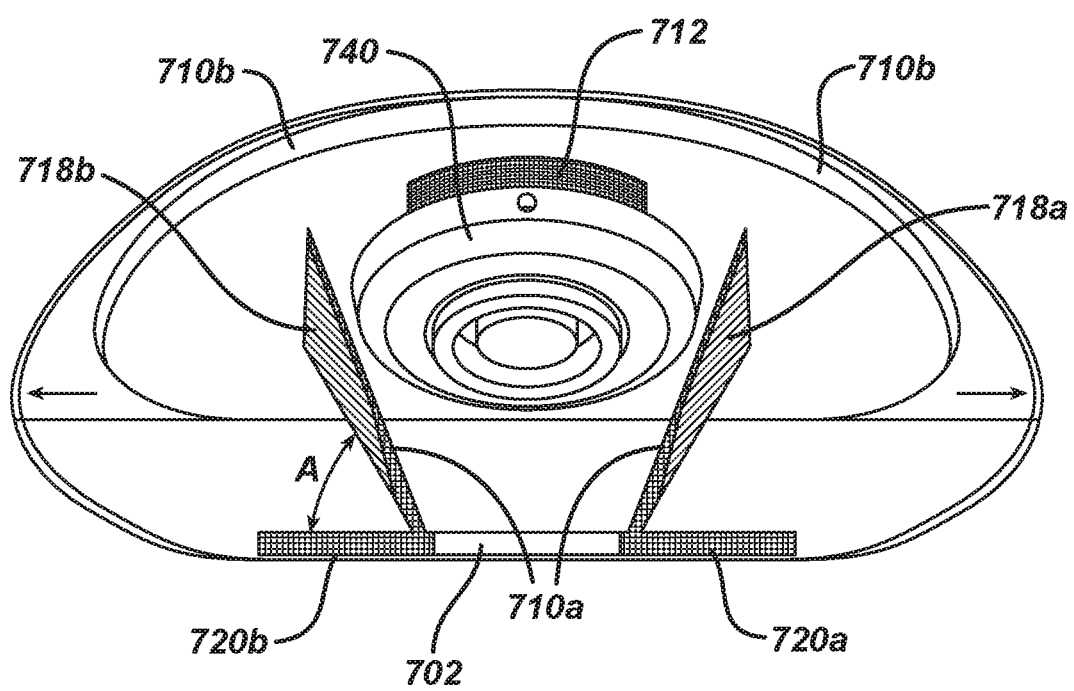
Figure 7C:
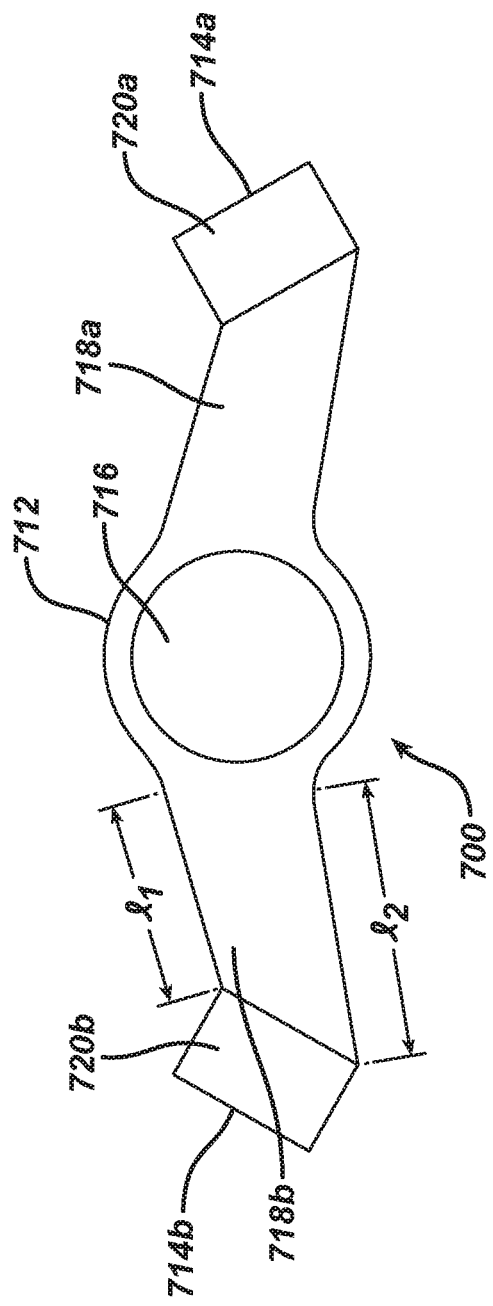
FIG. 7c is a plan view illustrating the vertical tether member of FIGS. 7a and 7b.

Although the tether may have various suitable configurations, one specifically advantageous embodiment is shown in greater detail with reference to FIGS. 7b and 7c. Referring first to FIG. 7c, a preferred vertical tether member 700 includes a first end 714a and a second end 714b, and a central region 712 therebetween. The central region 712 is secured to the anterior face of the implant, and preferably includes an opening 716 therethrough that is sized and shaped to fit around the injection port or self-sealing zone 740. Between the central region 712 and the first end 714a is a first vertical portion 718a and a first posterior face portion 720a. Similarly, between the central region 712 and the second end 714b is a second vertical portion 718a and a second posterior face portion 720b. As best shown in FIG. 7b, the first and second posterior face portions 720a, 720b lie flush against the posterior face 702 of the implant, and are secured thereto by any suitable means to anchor the first and second ends to the posterior face. Exemplary suitable means include, but are not limited to, using un-vulcanized silicone sheeting and heat, silicone based adhesives, solvent-based bonding, diffusion bonding, ultrasonic welding, laser spot welding, and other techniques know to a skilled artisan. A vertical tether extending between the injection port or self-sealing area 740 and the posterior face 702 of the implant aids in restricting undesired upper pole expansion by redirecting expansion to the lower pole where it is desired.

In the embodiment illustrated in FIG. 7b, the first and second posterior face portions are substantially rectangular in shape and are secured to the posterior face of the implant at a location such that the first and second vertical portions 718a, 718b of the vertical tether member extend to the anterior face of the implant at an angle A of less than 90 degrees, and preferably between 25 and 70 degrees. In other words, the vertical tether members extend upwardly and in a lateral direction toward the periphery of the implant (indicated by the arrow in FIG. 7b) so as to form an acute angle A. Angling the first and second vertical portions inward to a more central location on the posterior face enables the posterior face to maintain a flatter position and prevents curling of the expander that might otherwise happen if the anchoring points were closer to the periphery of the posterior face. Curling can render the posterior face unstable and subject to undesired movement and even flipping while implanted. It also can leave the implant prone to unintended expansion profiles. Minimization of posterior curling may also result in more even pressure distribution to the chest wall.

Figure 7D:
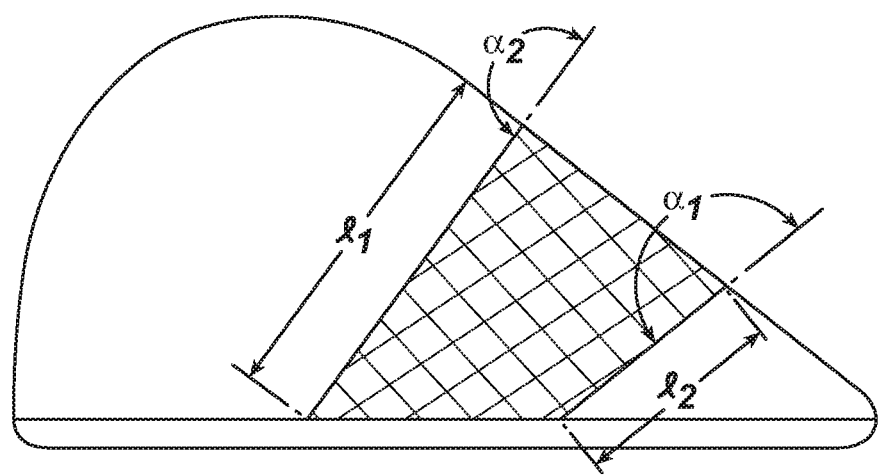
FIG. 7d is a side view of an implant illustrating only positioning of the vertical tether member for illustrative purposes.

Referring now to FIG. 7d, the lengths $l_1$, $l_2$ of the respective sides of each of the first and second vertical portions are shown, as are angles $\alpha_1$ and $\alpha_2$ representing the angle at which the vertical portions extend into the implant relative to a line perpendicular to the surface of the implant as shown. According to a preferred embodiment of a relatively large implant, such as an 850 cc implant, length $l_1$ is 37.9 mm and $l_2$ is 46.7 mm, and $\alpha_1$ is 128.8 degrees and $\alpha_2$ is 132.6 degrees. For a relatively small implant, such as a 350 cc implant, length $l_1$ is 24.2 mm and $l_2$ is 39.82 mm, and $\alpha_1$ is 161.52 degrees and $\alpha_2$ is 181.15 degrees. Although exemplary designs are set forth above, it is to be understood that they are not meant to be limiting examples, as it is intended that the scope of the invention be limited only by the appended claims.

As is also shown in FIGS. 7a and 7b, the insert member 600 has first and second slit-like apertures 710a, 710b therein that are sized and shaped to allow passage therethrough of the first and second vertical portions 718a, 718b of the vertical tether.

The vertical tether member made of any suitable material having an elasticity that is suitable to increase the shell's resistance to outward expansion, such as Dacron™, polypropylene, Dacron™-silicone composite etc.

Although the embodiment described here includes a central region extending to both first and second ends that each attach to the posterior face of the implant, it is envisioned that the vertical tether member may alternatively extend from the central region to only a single point of attachment to the posterior face.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. An expandable mammary tissue implant comprising:
    an inflatable shell having an anterior face and a posterior face having a periphery, the anterior face having an upper pole region and a lower pole region meeting at an apex, and an injection zone for receiving fluid therethrough to inflate the implant, the upper pole region being an upper portion of the shell when an implant recipient is standing and the lower pole region being a lower portion of the shell when the implant recipient is standing;
    a first reinforcing sheet coupled to the shell and extending around the entire periphery of the posterior face, the first reinforcing sheet having a peripheral rim portion extending upward from the periphery of the posterior face into the anterior face by a predetermined distance to an upper periphery of the first reinforcing sheet such that the first reinforcing sheet does not extend along the entire anterior face;
    a second reinforcing sheet coupled to the shell and extending along only the anterior face of the shell from the upper pole region to near the apex:
    wherein the first reinforcing sheet overlaps or abuts the second reinforcing sheet only at or adjacent the upper periphery of the first reinforcing sheet in the upper pole region such that the upper pole region is entirely reinforced as between the first and second reinforcing sheets and wherein a portion of the lower pole region is not reinforced by either the first or second reinforcing sheets.

2. The expandable implant according to claim 1, further comprising a vertical tether member having a first end, a second end and a central region therebetween having an aperture therethrough, wherein the central region is coupled to the anterior face of the implant at a location such that the injection zone is positioned within the aperture in the central region, and wherein the first and second ends of the vertical tether member are coupled to the posterior face of the implant.

3. The expandable implant according to claim 2, wherein the vertical tether member is comprised of a mesh material.

4. The expandable implant according to claim 3, wherein the mesh material is a polyester mesh.

5. The expandable implant according to claim 4, wherein the shell is comprised of silicone.

6. The expandable implant according to claim 1, further comprising
at least one insert member positioned entirely within and extending across an interior of said shell, and coupled to an interior of said shell around an entire perimeter of said insert member at a location adjacent to the upper periphery of said first reinforcing sheet.

7. The expandable implant according to claim 6, wherein the at least one insert member has at least first and second apertures therein, and wherein the first and second ends of the vertical tether member extend through said respective first and second apertures.

8. The expandable implant according to claim 2, wherein the vertical tether member further includes first and second posterior face portions adjacent the first and second ends respectively, and first and second vertical portions extending between the central portion and first and second posterior face portions respectively, wherein the entirety of the first and second posterior face portions are coupled to the posterior face of the implant.

9. The expandable implant according to claim 8, wherein the first and second posterior face portions are coupled to the posterior face of the implant at a location such that the first and second vertical portions extend toward the anterior face at an acute angle relative to the first and second posterior face portions.

10. An expandable mammary tissue implant comprising:
a shell having an anterior face and a posterior face, the anterior face having an upper pole region and a lower pole region meeting at an apex, and an injection zone for receiving fluid therethrough to inflate the implant;
a vertical tether member having a first end, a second end, a first vertical portion, a second vertical portion and a central region between the first and second vertical portions, the central region having an aperture therethrough, wherein the central region is coupled to the anterior face of the implant at a location such that the injection zone is positioned within the aperture in the central region, and wherein the first and second ends of the vertical tether member are coupled to the posterior face of the implant such that the first and second vertical portions extend across an interior of said shell from the anterior face to the posterior face;
a reinforcing material coupled to the shell in a first reinforcement zone, the reinforcing material having a peripheral rim portion extending upward from a periphery of said posterior face into the anterior face by a predetermined distance to an upper periphery of the reinforcing material;
at least one insert member, the at least one insert member being at least one sheet of material positioned entirely within and extending across the interior of said shell transverse to the first and second vertical portions, and coupled to the interior of said shell around at least a portion of a perimeter of said insert member at a location adjacent to the upper periphery of the reinforcing material;
wherein the insert member has at least first and second apertures therein, and wherein the first and second vertical portions of the vertical tether member extend through said respective first and second apertures.

* * * * *